United States Patent [19]

Ozaki et al.

[11] Patent Number: 5,264,605
[45] Date of Patent: Nov. 23, 1993

[54] MYOINSITOL DERIVATIVES, PROCESS FOR PREPARING SAME, PHOSPHORYLATING AGENT, AND ITS UTILIZATION

[75] Inventors: Shoichiro Ozaki; Yutaka Watanabe, both of Matsuyama, Japan

[73] Assignee: Mitsui Toatsu Chemicals, Incorporated, Tokyo, Japan

[21] Appl. No.: 651,368

[22] PCT Filed: Jun. 27, 1990

[86] PCT No.: PCT/JP90/00834
§ 371 Date: Feb. 20, 1991
§ 102(e) Date: Feb. 20, 1991

[87] PCT Pub. No.: WO91/00258
PCT Pub. Date: Jan. 10, 1991

[30] Foreign Application Priority Data

Jun. 28, 1989 [JP] Japan .................................. 1-167351
Mar. 10, 1990 [JP] Japan .................................. 2-58453

[51] Int. Cl.$^5$ ............................ C07F 7/08; C07F 7/18
[52] U.S. Cl. ........................... 556/437; 556/443; 556/449; 556/482; 560/106; 560/182; 560/198; 558/122
[58] Field of Search ............... 556/437, 449, 482, 443; 560/106, 182, 188; 558/122

[56] References Cited

U.S. PATENT DOCUMENTS 4,801,597 1/1989 Stacpoole ........................... 514/332
4,988,682 1/1991 Kozikowski ....................... 568/833

OTHER PUBLICATIONS

Journal of the Chemical Society, Chemical Communications, No. 8, 1989, pp. 482–483, Y. Watanabe et al.

Primary Examiner—Paul F. Shaver
Attorney, Agent, or Firm—Nixon & Vanderhye

[57] ABSTRACT

A process for preparing myoinositol polyphosphoric acid from myoinositol via a polyacylmyoinositol, a process for preparing a polysilyl-polyacylmyoinositol from a polyacylmyoinositol, and a process for preparing an optically active myoinositol polyphosphoric acid from the above product or a polysilylmyoinositol.

5 Claims, 10 Drawing Sheets

MYOINSITOL DERIVATIVES, PROCESS FOR PREPARING SAME, PHOSPHORYLATING AGENT, AND ITS UTILIZATION

DESCRIPTION

1. Technical Field

The present invention relates to myoinositol derivatives having a probability that they will be used as medicines, a process for synthesizing the same, a novel phosphorylating agent represented by the formula (I)

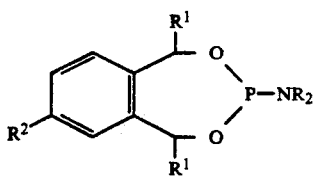

and its application.

2. Background Art

A simple process for the synthesis of myoinositol polyphosphoric acid has not been found. Furthermore, an easily usable phosphorylating agent for the hydroxyl groups of myoinositol has not been found.

In addition, a simple process for the synthesis of myoinositol polyphosphoric acid, an optical resolution of a myoinositol derivative and an advantageous process of an optical activator have not been found.

DISCLOSURE OF THE INVENTION

There are here disclosed a process for preparing a polyacylmyoinositol by reacting myoinositol with an acyl halide, a process for preparing a polyacyl-myoinositol, a short process for easily preparing myoinositol polyphosphoric acid from a polyacyl-myoinositol in a high yield, a process for preparing a polysilyl polyacylmyoinositol by reacting a polyacyl-myoinositol with a silylating agent, a process for easily preparing myoinositol polyphosphoric acid in a high yield by reacting a polysilylmyoinositol or a polysilyl-polyacylmyoinositol with a phosphorylating agent, a process for preparing an optically active myoinositol polyphosphoric acid in accordance with these processes, an easy optical resolution of these products, and various intermediates in these processes.

BRIEF DESCRIPTION OF THE DRAWINGS

All of FIGS. 1 to 10 show synthetic processes of the present invention. Of these drawings.

BEST MODE FOR CARRYING OUT THE INVENTION

It is considered that when myoinositol is subjected to acylation, six hydroxyl groups are acylated substantially randomly However, it has been found that a 1,3,4,5-tetraacyl compound and a 1,3,5-triacyl compound can be produced in overwhelmingly large quantities under certain conditions. Furthermore, it has also been found that a 1,4,5-triacyl compound as well as other various polyacyl compounds can be obtained by changing the conditions. The utilization of these polyacylated myoinositols permits synthesizing myoinositol polyphosphoric acid.

Figure 1:
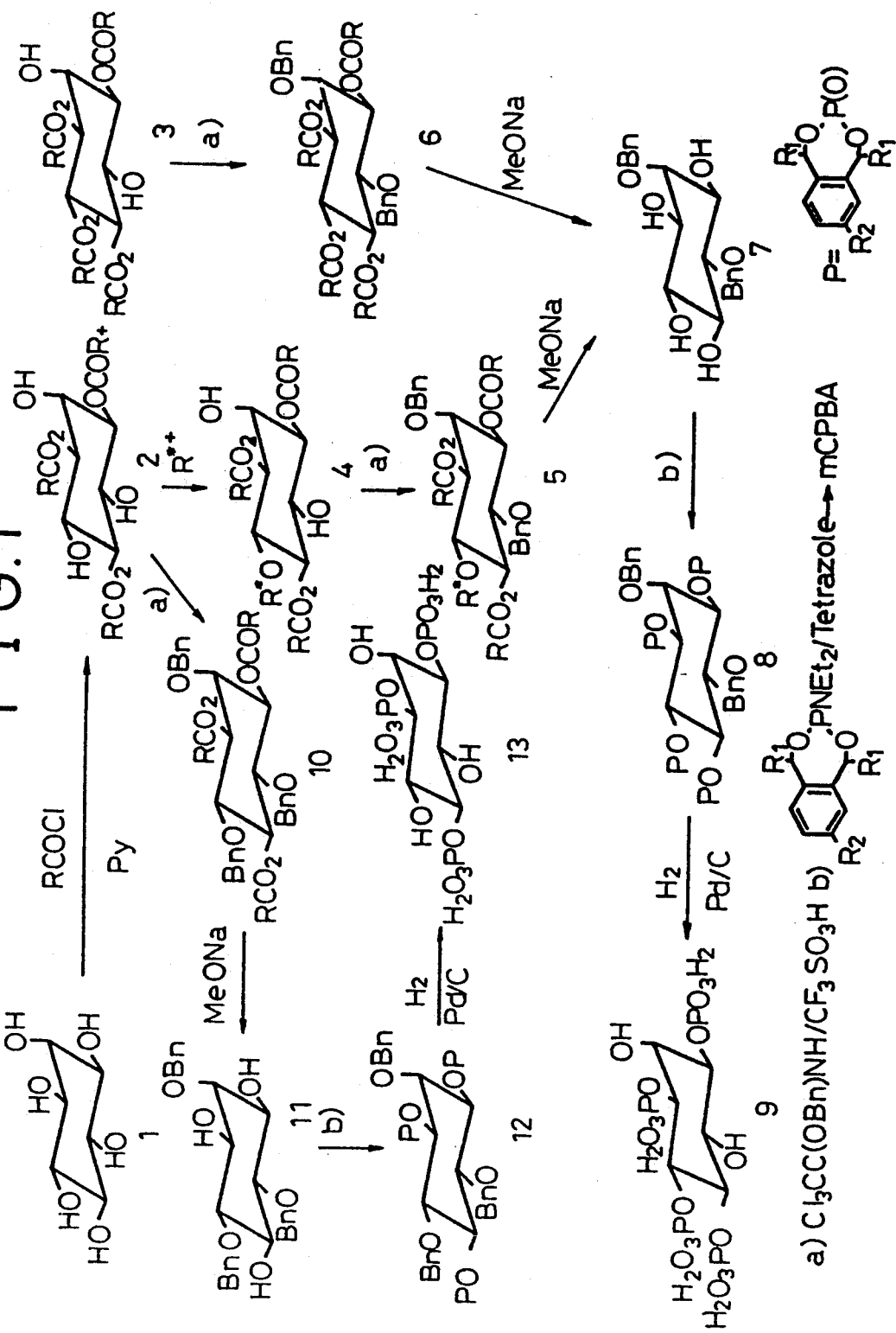

Explanation will be made in reference to FIG. 1 as an example.

Myoinositol is reacted with an acyl halide in order to obtain a 1,3,5-triacyl compound 2 and a 1,3,4,5-tetraacyl compound 3. This 1,3,5-triacyl compound 2 is then reacted with R*X so as to introduce R* into the 4 position, thereby synthesizing a compound 4. Next, optical resolution is carried out, and the 2 and 4 positions of the compound are benzylated to obtain a compound 5. This compound 5 is then reacted with an alkali, so that the acyl groups at the 1, 3 and 5 positions of the compound 5 and the R* at the 4 position thereof are eliminated therefrom, in order to obtain a compound 7. On the other hand, reduction eliminable protective groups are introduced into the 2 and 6 positions of the 1,2,4,5-tetraacyl compound 3 in order to obtain a compound 6. This compound 6 is then reacted with a base to obtain a compound 7. This compound 7 is further reacted with a suitable phosphorylating agent, thereby obtaining a compound 8. Afterward, this compound 8 is subjected to catalytic reduction in order to obtain myoinositol 1,3,4,5-tetraphosphate 9.

On the other hand, suitable protective groups are introduced into the 2, 4 and 6 positions of the triacyl compound 2 to obtain a compound 10, and the acyl groups of the compound 10 are eliminated to obtain a compound 11. This compound 11 is then subjected to phosphorylation, thereby obtaining a compound 12, and this compound 12 is catalytically reduced in order to obtain myoinositol-1,3,5-triphosphoric acid.

Examples of the acyl halide include combinations of aliphatic and aromatic acyl groups having 2 to 20 carbon atoms and halogens of chlorine, bromine, fluorine and iodine, and the most suitable example is benzoyl chloride. The reaction of the acyl halide is carried out in a suitable solvent such as pyridine.

Examples of the protective groups for the hydroxyl groups which are free from the acyl groups include benzyl, substituted benzyl, p-methoxybenzyl and allyl. The protective group can be prepared by adding benzyl chloride, o-benzyl trichloroacetoimidate or allyl chloride. The benzyl group which can undergo catalytic hydrogenolysis is most suitable.

For the elimination of the acyl group or R*, a base such as CH$_3$ONa can be used.

Examples of the usable phosphorylating agent include, in addition to the phosphorylating agents represented by the formula (I), tetrabenzyl pyrophosphate, dianilinophosphoric acid chloride and di(benzyloxy)-phosphodiethylamide. Usually, the release of the phosphorylated compound from protection can be suitably achieved by catalytic hydrogenolysis by the use of Pd/C as a catalyst. Examples of R* which is introduced into the 4 position of the compound 2 include methoxyacetyl, methoxymethyl, p-methoxybenzyl and camphaloyl, and a reagent containing R* is usually R*X wherein X is a halogen. The compound 4 into which R* is introduced is of a d.l form, and optical resolution is possible. This optical resolution can be achieved by the use of a column or a Chiral column or by means of recrystallization.

When the acylation is carried out at a high temperature, the selectivity of the acylation deteriorates, so that 14% of a 1,3,4,5,6-pentabenzyl compound, 37% of a 1,3,4,5-tetrabenzoyl compound, 7.3% of 1,3,4,6-tetrabenzoyl compound, 0.58% of 1,5,6-tribenzoyl compound and 0.61% of 1,5-dibenzoyl compound were produced. When these polyacyl compounds are used as raw materials in accordance with the above-mentioned process or a procedure described in the undermentioned example, myoinositol polyphosphoric acid can be obtained in which phosphate groups are introduced into positions of the acyl groups. For example, myoinositol 1,4,5-triphosphoric acid can be obtained from 1,4,5-tribenzoyl myoinositol.

Figure 2:
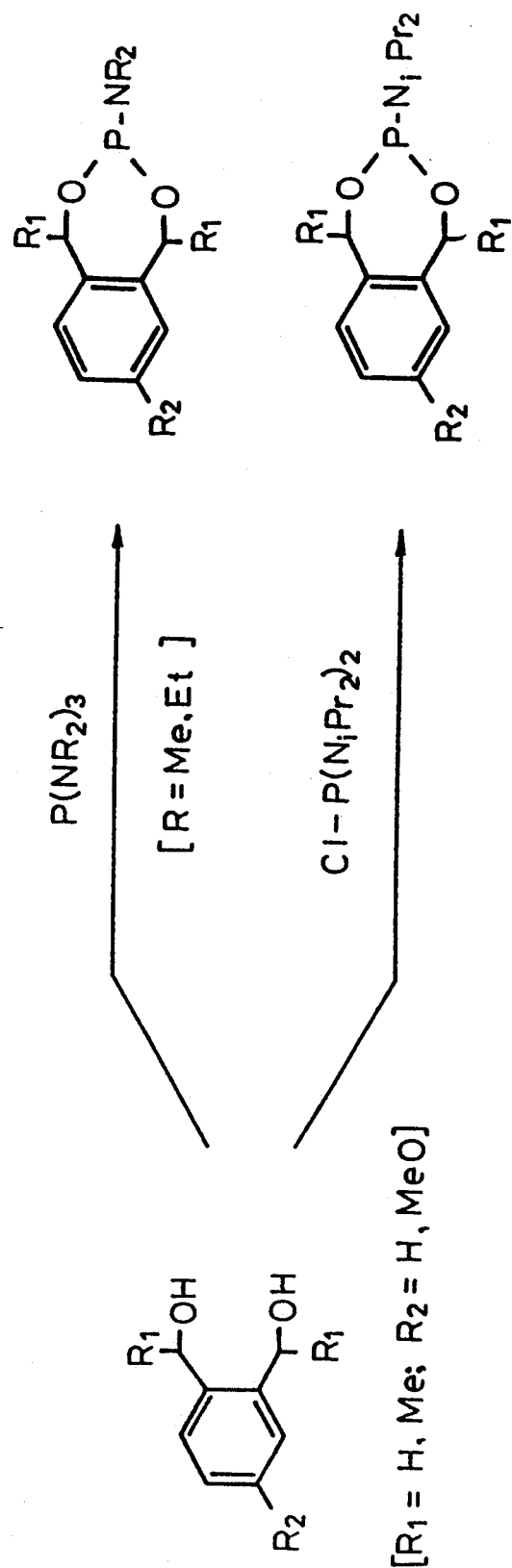

Of compounds represented by the formula (I) used in the phosphorylation, some compounds are only known in which R is methyl or ethyl and each of $R^1$ and $R^2$ is hydrogen. However, the present inventors have newly synthesized several usable compounds, for example, in which R is isopropyl and both of $R^1$ and $R^2$ are hydrogen, in which R is ethyl, $R^1$ is methyl, $R^2$ is hydrogen, and in which R is ethyl, $R^1$ is hydrogen and $R^2$ is methoxy. The compound in which R is isopropyl cannot be synthesized by the same process as in the case of the compound in which R is methyl or ethyl, and it could be synthesized for the first time by reacting phthalyl alcohol with bisdiisopropylaminochlorophosphine, as shown in FIG. 2.

Figure 3:
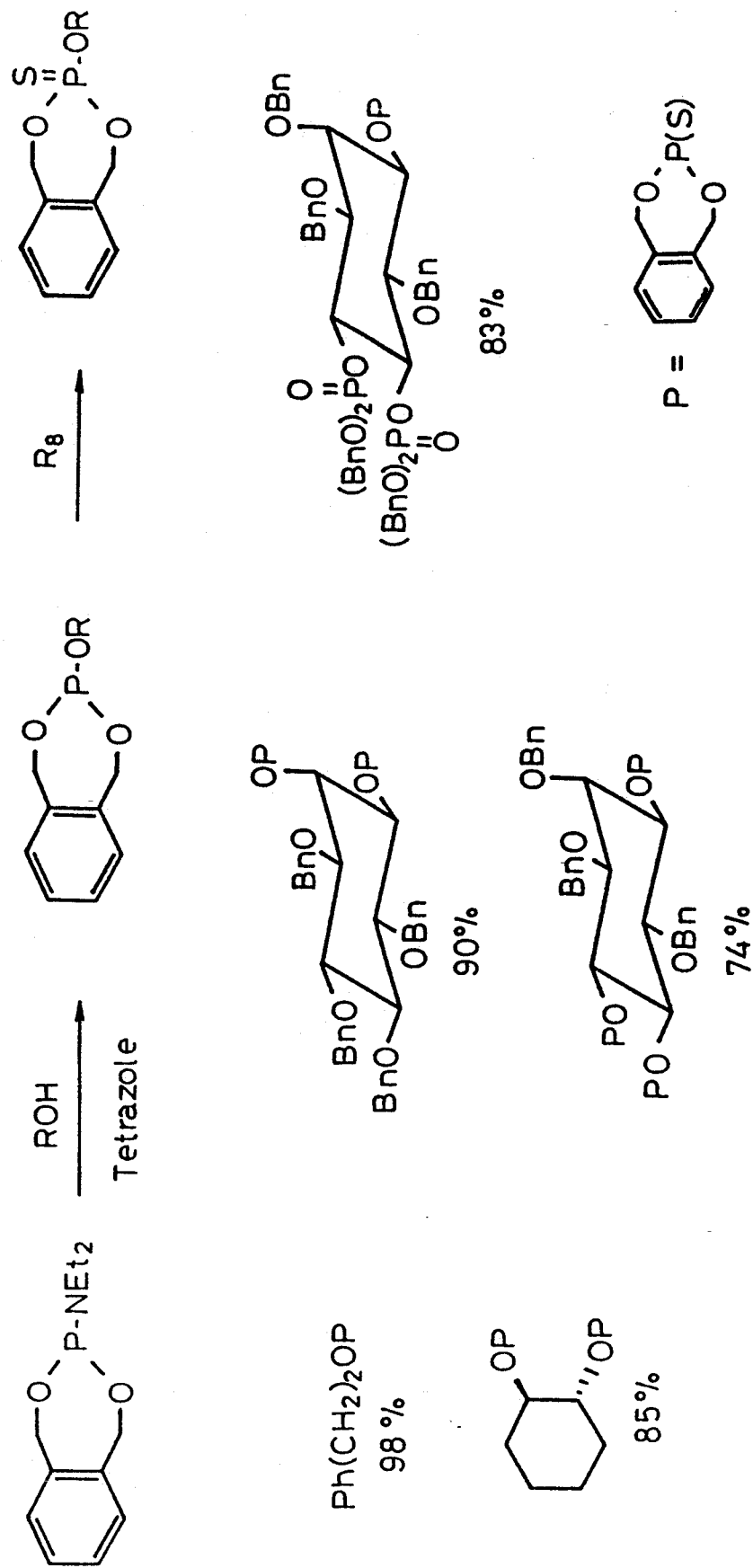

The compound represented by the formula (I) in which R is methyl or ethyl is known, but the research on the reaction thereof has not been conducted at all. The reaction the compound of the formula (I) with the hydroxyl group of myoinositol has been researched for the first time by the present inventors. In consequence, they have found a technique by which the hydroxyl groups of myoinositol can be phosphorylated extremely easily in a high reproducibility in a high yield. Myoinositol is oxidized with mCPBA (m-chloroperacetic acid) in order to become a pentavalent phosphorus compound. Furthermore, after the phosphorylation with the compound represented by the formula (I) of the present invention, oxidation with sulfur can easily be achieved. In this case, sulfur is bonded to phosphorus, and the valence of phosphorus changes from trivalence to pentavalence, as shown in FIG. 3.

The first of the other aspects of the present invention is connected to a process which comprises the steps of subjecting myoinositol to polyacylation, silylating the remaining hydroxyl groups, removing all or a part of the acyl groups, and then phosphorylating hydroxyl groups which are formed after the above-mentioned removal.

In the first place, this invention will be described in reference to the process using 1,3,4,5-tetrabenzoyl-myoinositol (101) as a raw material.

Figure 4:
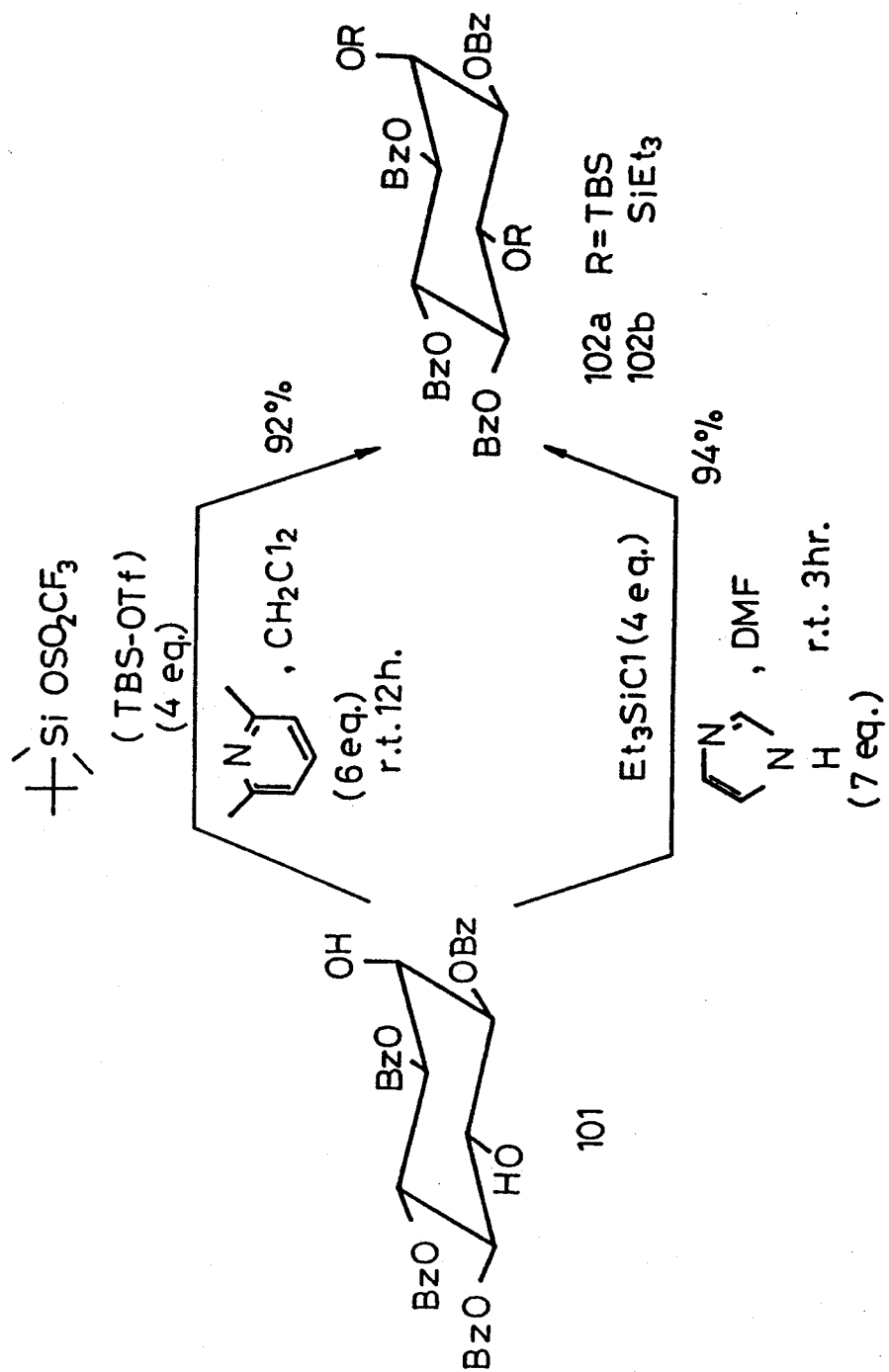

In FIG. 4, 1,3,4,5-tetrabenzoyl-myoinositol is silylated with dimethyl-t-butylsilyl triflate or triethylsilyl chloride in order to form 2,6-bis(dimethyl-t-butylsilyl)-1,2,4,5-tetrabenzylmyoinositol (102b) or 2,6-bis(triethylsilyl)-1,3,4,5-tetrabenzoylmyoinositol (102b), respectively.

Figure 5:
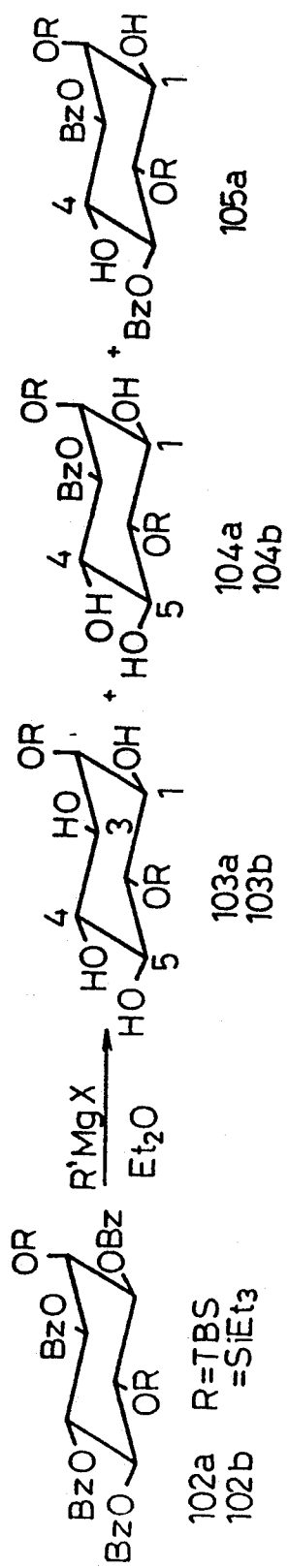
FIG. 5 shows the removal of benzoyl groups by the use of a Grignard reagent.

As in FIG. 5, the compound 102a or 102b is reacted with a Grignard reagent such as ethylmagnesium bromide, so that all or a part of the benzoyl groups are eliminated therefrom in order to form 2,6-bis(dimethyl-t-butylsilyl)-myoinositol (103a), 2,6-bis(dimethyl-t-butylsilyl)-3-benzoyl-myoinositol (104a), 2,6-bis(dimethyl-t-butylsilyl-3,5-dibenzoyl-myoinositol (105a) as well as 2,6-bis(triethylsilyl)-myoinositol (103b) and 2,6-bis(triethylsilyl)-3-benzoyl-myoinositol (104b), respectively.

Figure 6:
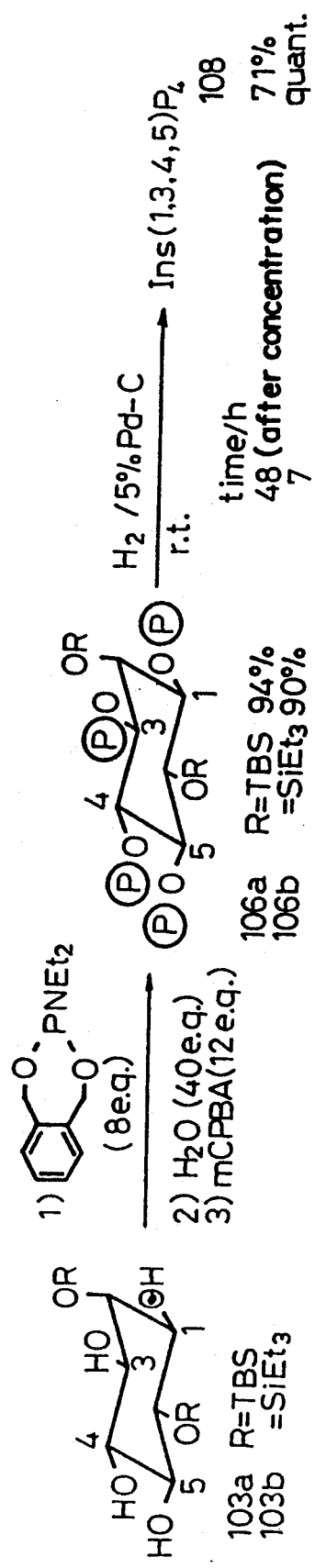
FIG. 6 shows the synthesis of Ins(1,3,4,5)P$_4$ and Ins(1,4,5)P$_3$.
Figure 6:
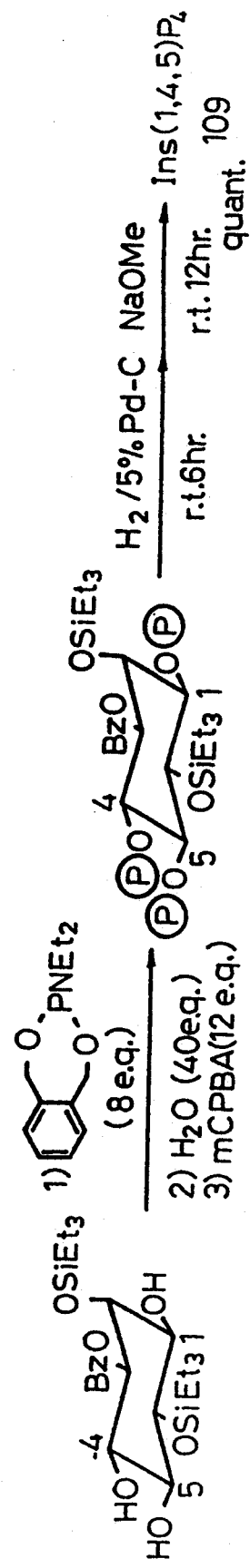

In FIG. 6, the compound 103a is reacted with 3-diethylamino-2,4,3-benzodioxaphosphepine in order to obtain 2,6-bis(dimethyl-t-butylsilyl)-1,3,4,5-tetrakis(1',5'-dihydro-2',4',3'-benzodioxaphophepinyl)-inositol (106a). Furthermore, the compound 103b is phosphorylated in like manner in order to obtain 2,6-bis(triethylsilyl)1,3,4,5-tetrakis(1',5'-dihydro-2',4',3'-benzodioxaphosphepinyl)myoinositol (106b).

The compound 104b is phosphorylated in like manner to obtain 2,6-bis(triethylsilyl)-3-benzoyl-1,4,5-tris(1',5'-dihydro-2',4',3'-benzodioxaphosphepinylmyoinositol (107b).

The compound 106 is subjected to catalytic hydrogenolysis by the use of palladium-carbon as a catalyst to obtain myoinositol-1,3,4,5-tetraphosphoric acid (108). Furthermore, the compound 107b is subjected to catalytic hydrogenolysis and then an alkali treatment in order to obtain myoinositol-1,4,5-triphosphoric acid (109).

The second aspect of the present invention is directed to the preparation of an optically active compound.

When a polyacyl compound is produced from myoinositol as a raw material which is a meso form compound, the resulting polyacyl-myoinositol is a racemic modification or a meso form compound. It has been found that when the above polyacyl-myoinositol is reacted with a compound which can be formed by treating two hydroxyl groups of tartaric monoester with ketal, an optically active compound can be obtained.

Figure 7:
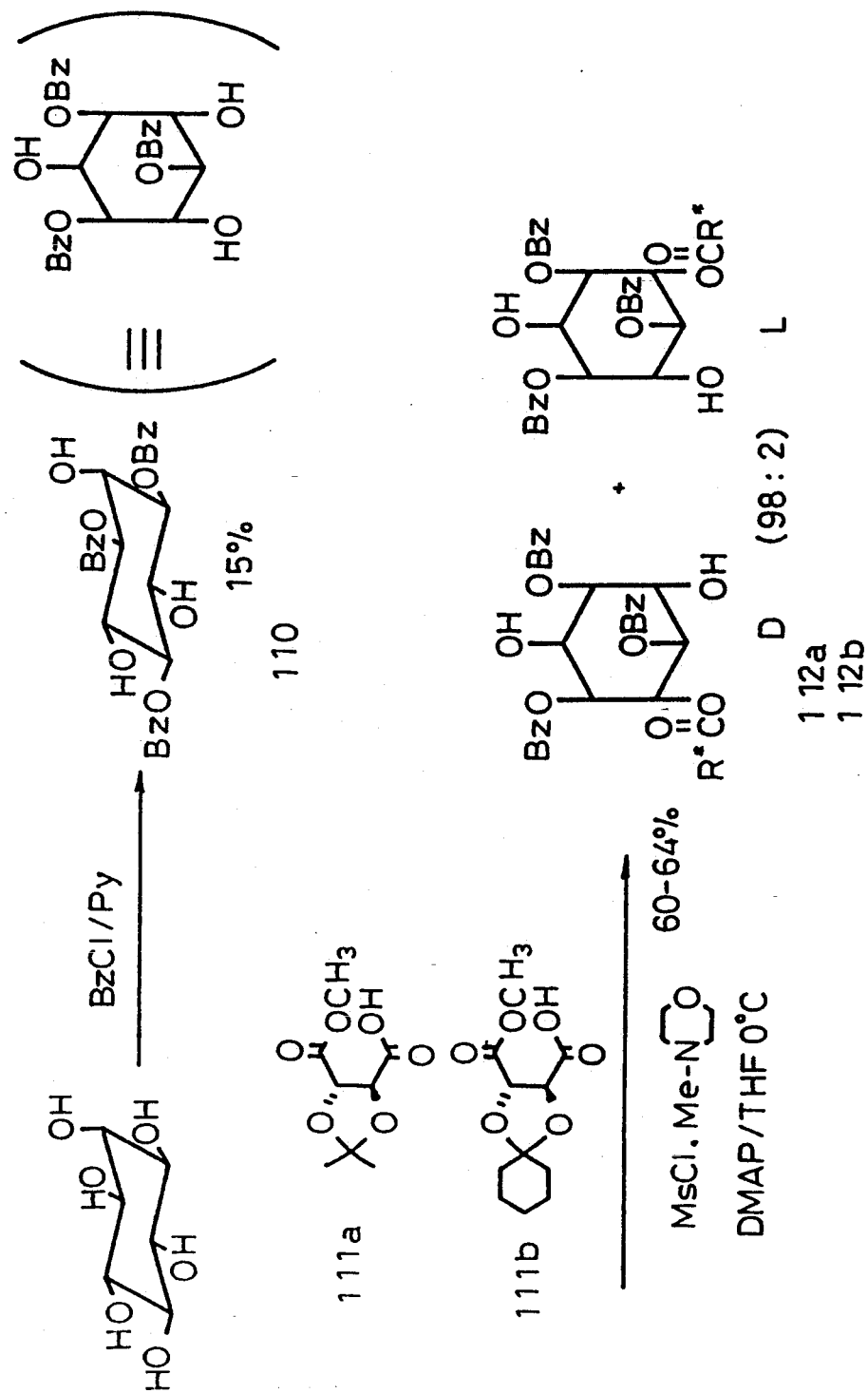
FIG. 7 shows an asymmetric esterification of 1,3,5-tri-0-benzoyl-myoinositol.
Figure 8:
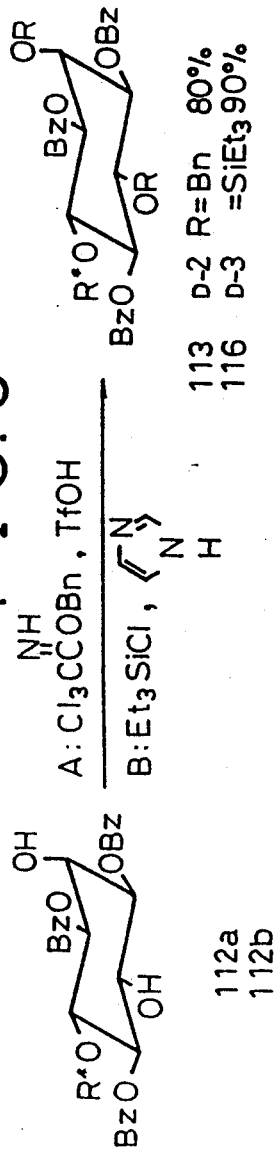
FIG. 8 shows the synthesis of optically active Ins(1,3,4,5)P$_4$ and Ins-(1,4,5)P$_3$.
Figure 8:
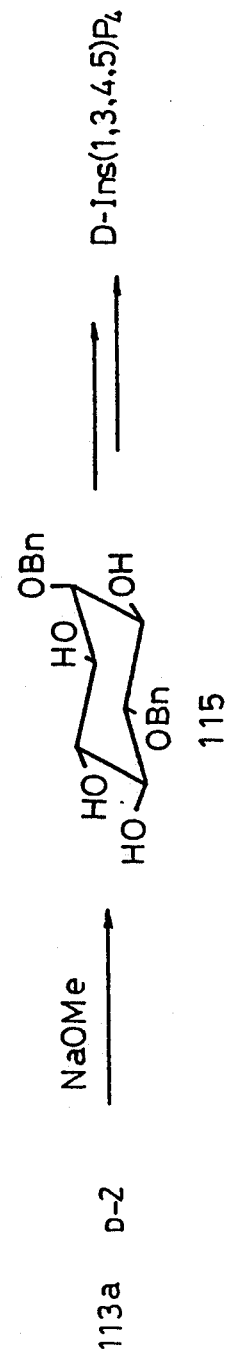
Figure 8:
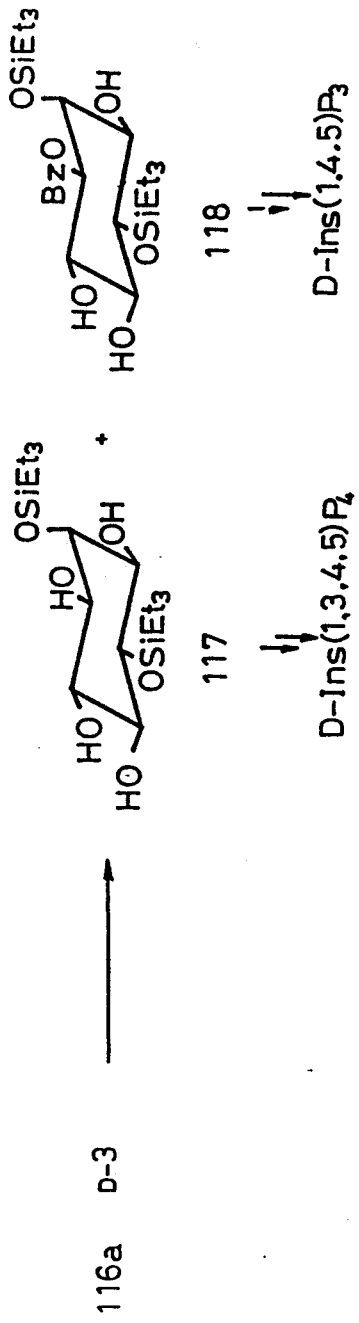

In FIG. 7, D-2,3-O-cyclohexylidene D tartaric acid monomethyl ester (111b) is reacted with 1,3,5-tribenzoylmyoinositol (110) which is of a meso form in order to sterically selectively acylate the hydroxyl group at the 4 position, whereby 98% of D-1,3,5-tribenzoyl-4-(methyl-2',3'-O-cyclohexylidene-D-tartaroyl)-myoinositol (112b) and 2% of a L-compound (96% de) can be obtained In FIG. 8, the compound (112b) is treated with benzyl trichloroacetoimidate in order to obtain 2,6-dibenzyl-1,3,5-tribenzoyl-4-(methyl-2',3'-O-cyclohexylidene-D-tartaroyl)-myoinositol (113b) in which both of the 2 and 6 positions are benzylated as well as 6-benzyl-1,3,5-tribenzoyl-4-(methyl-2',3'-O-cyclohexylidene-D-tartaroyl)-myoinositol (114b) in which the 6 position is only benzylated. The compound 113b is treated with sodium methylate to obtain D-2,6-dibenzylmyoinositol (115). This compound 115 is then treated with 1,5-dihydro-3-diethylamino-2,4,3-benzodioxaphosphepine, followed by oxidation and catalytic reduction, in order to D-myoinositol(1,3,4,5)tetraphosphic acid. Furthermore, the compound 114b is treated in like manner to obtain D-myoinositol(1,2,3,4,5)pentaphosphoric acid.

1,3,5-tribenzoyl-4-(methyl-2',3'-O-isopropylidene-D-tartaroyl)-myoinositol is reacted with triethylsilyl chloride to obtain 2,6-bis(triethylsilyl)-1,3,5-tribenzoyl-4-(methyl-2',3'-O-isopropylidene-D-tartarolyl)-myoinositol (116b). This compound 116b is then reacted with ethylmagnesium bromide to obtain 2,6-bis(triethylsilyl)-D-myoinositol (117) and 2,6-bis(triethylsilyl)-3-benzoyl-D-myoinositol (118). The compounds 117 and 118 are then subjected to phosphorylation, oxidation and an alkali treatment, thereby obtaining optically active D-myoinositol(1,3,4,5)tetraphosphoric acid and D-myoinositol(1,4,5)triphosphoric acid, respectively.

Figure 9:
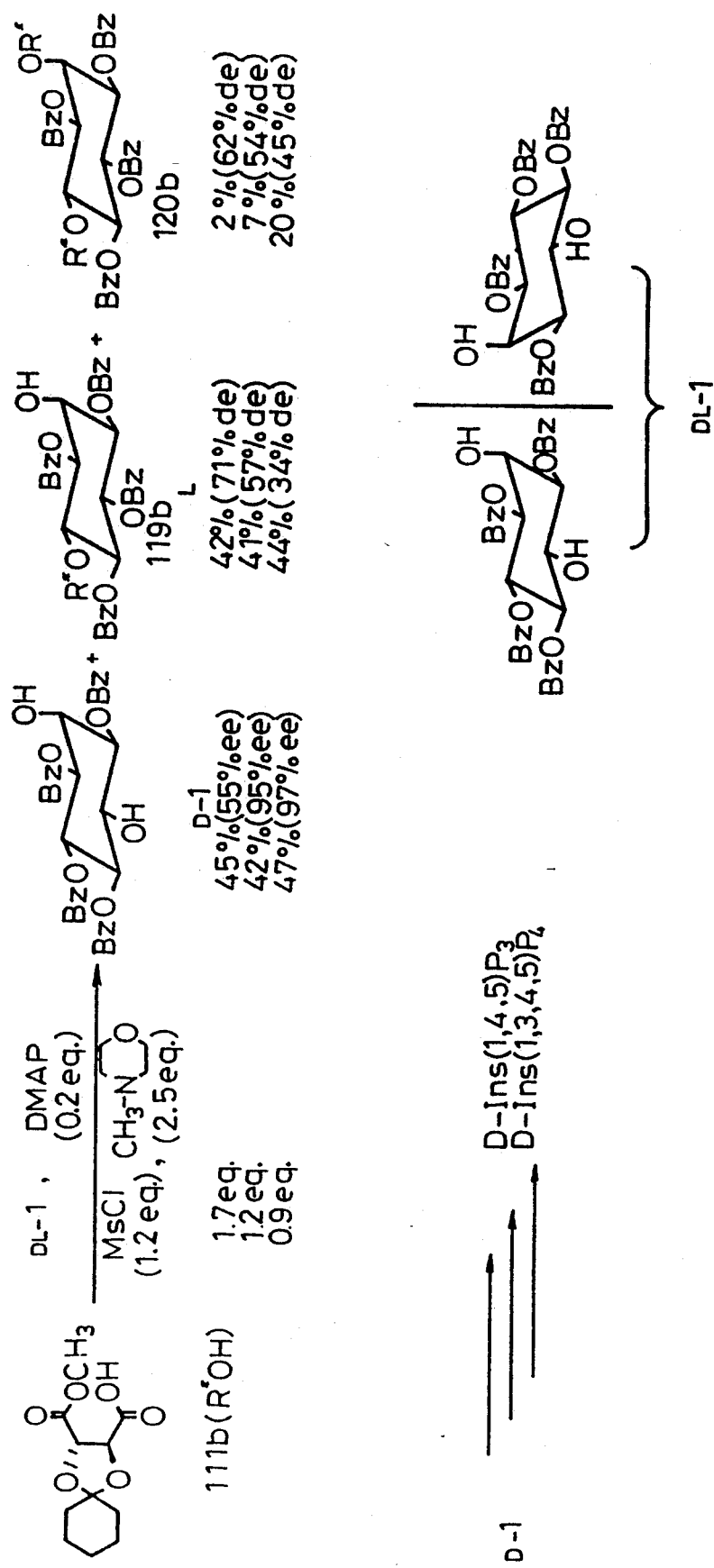
FIG. 9 shows the preparation of D-1,3,4,5-tetra-O-benzoyl-myoinositol by means of kinetic optical resolution.

As shown in FIG. 9, the third aspect of the present invention is directed to a process for preparing an optically active compound from a racemic modification. 1,3,4,5-tetrabenzoyl-myoinositol which is a mixture (racemic modification) of D and L is treated with a derivative 111b of tartaric acid. In this case, it has been found that the D form compound only remains as the unreacted material (D-1) and that the compound L-1 having the L form only reacts in order to produce 1,3,5,6-tetrabenzoyl-4-(methyl-2',3'-O-cyclohexylidene-D-tartaroyl)-myoinositol (119b) and 1,3,5,6-tetrabenzoyl- 2,4-bis(methyl-2',3'-O-cyclohexylidene-D-tartaroyl)myoinositol (120b). The compound D-1 can be utilized to synthesize optically active D-myoinositol(1,3,4,5)P$_4$ and D-myoinositol(1,4,5) in accordance with the processes in FIGS. 4 and 5.

The process of the present invention is not limited to the procedures shown in these figures, and in place of the benzoyl group, an acyl group such as acetyl, propionyl, toluoyl or naphthoyl can be used.

Examples of the silylating agent include trimethyl halides, dimethylethylsilyl halides, dimethyl-i-butylsilyl halides, dimethylpropylsilyl halides, tripropylsilyl halides and tributylsilyl halides as well as triflate in addition to the above-mentioned triethylsilyl chloride and dimethyl-t-butylsilyl chloride.

In removing the acyl group, a Grignard reagent is used.

Examples of the usable Grignard reagent include all of reagents which can be prepared by adding magnesium to halides having alkyl groups such as methyl, propyl and butyl and aryl groups such as phenyl and tolyl, in addition to ethylmagnesium bromide. Furthermore, besides these Grignard reagents, there can also be used sodium alkoxides, LiAlH, NaBH$_4$ and reducing agents for esters such as a combination of an alcohol and sodium. The above-mentioned silylation and Grignard reaction can be carried out at a usual reaction temperature in a usual solvent.

Examples of the phosphorylating agent include diethylamino-dicyanoethylphosphine, a trivalent phosphorus compound such as phosphorus trichloride, tetrabenzylpyrophosphoric acid and dianilinophosphoric acid chloride in addition to 3-diethylamino-2,4,3-benzodioxaphosphepine. When trivalent phosphorus is used, the oxidation is made by the use of mCPBA, t-butylhydro peroxide or the like.

In the last place, the catalytic reduction is effected with hydrogen in order to lead to free phosphoric acid.

For convenience, myoinositol is represented by I, a benzoyl group by Bz, a phosphoric acid derivative by P, a silicon derivative by Si, and a tartaric acid derivative by T.

When an L-tartaric acid derivative is used, phenomena which are directly opposite to the case of the D form tartaric acid are perceived in the cases of I(1,3,5)Bz (10) and I(1,3,4,5)Bz (D, L-1), and L-I(1,4,5)P$_3$ and L-I(1,3,4,5)P$_4$ can be obtained.

Also in case that monomethyl ester is replaced with monoethyl ester as the tartaric acid derivative, a similar effect can be observed. Cyclohexylidene can be replaced with cyclopentylidene, cycloheptylidene, dimethylsilylidene in which in place of carbon, silicon is bonded to two oxygen atoms, or diethylsilylidene. When 2',3'-O-isopropylidene-2',3'-O-cyclohexylidene is replaced with tartaric acid having a non-closed 2',3'-O-benzoyl group, the effect is low, i.e., de is 24%.

Examples of the monoester of D- or L-tartaric acid in which oxygen atoms of two hydroxyl groups are bonded to one carbon or silicon include monoethyl ester of 2,3-O-isopropylidene-tartaric acid, 2,3-O-cyclohexylidenetartaric acid monopropyl ester, 2,3-dimethylsilylidenetartaric acid monomethyl ester and 2,3-O-diethylsilylidene tartaric acid monoethyl ester in addition to the above-mentioned ones.

The reaction of the hydroxyl group of the myoinositol derivative with the carboxyl group of tartaric acid can be achieved by the procedure for a usual esterification.

The above-mentioned process and conception are not limited to the preparation of I(1,3,4)P$_3$ and I(1,3,4,5)-P$_4$, but can be applied widely. For example, they can be applied to many acyl compounds obtained by the acylation of myoinositol, silyl compounds of the acyl compounds and benzyl compounds of the acyl compounds.

(1) IPx in which phosphate groups are introduced into the same positions as positions having the benzoyl groups can be synthesized in the order of IBzy, IBzySiz, ISiz, ISIzPx and IPx via the same route as in the preparation of the compounds 1, 2a, 3a, 6a and 8. The following compounds can be synthesized:

I(1,3,4,6)Bz$_2$, I(1,3,4,6)Bz$_4$, (2,5)Si$_2$, I(2,5)Si$_2$, I(2,5-)Si$_2$(1,3,4,6)P$_4$, I(1,3,4,6)P$_4$, I(1,3,4,5,6)Bz$_5$, I(1,3,4,5,6)Bz$_5$(2)Si, I(2)Si, I(2)Si(1,3,4,5,6)P$_5$, I(1,3,4,5,6)P$_5$, I(1,3,5)Bz$_3$, I(1,3,5)Bz$_3$(2,4,6)Si, I(2,4,6-)Si$_3$, I(2,4,6)Si$_3$, (1,3,5)P$_3$, I(1,3,5)P$_3$, I(1,4,5)Bz$_3$, I(1,4,5)Bz$_3$, (2,3,6)Si$_3$, I(2,3,6)Si$_3$, I(2,3,6)Si$_3$(1,4,5)P$_3$, I(2,3,4)Bz$_3$, I(1,3,4)Bz$_3$(2,5,6)Si$_3$, I(2,5,6)Si$_3$, I(2,5,6-)Si$_3$(1,3,4)P$_3$, I(1,3,4)P$_3$, I(1,5,6)Bz$_3$, I(1,5,6)Bz$_3$(2,3,4-)Si$_3$, I(2,3,4)Si$_3$, I(2,3,4)Si$_3$(1,5,6)P$_3$, I(1,5,6)P$_3$, I(1,5)Bz$_2$, I(1,5)Bz$_2$(2,3,4,6)Si$_4$, I(1,3,4,6)Si$_4$, I(2,3,4,6-)Si$_4$(1,5)P$_2$ and I(1,5)P$_2$.

(2) Application of partial silylation

When the compound 1 is silylated under conditions that the molar ratio of a silylating agent is 2 or less, 1,3,4,5-tetrabenzoyl-6-silyl-I (121) can be obtained. I(1,2,3,4,5)P5 can be synthesized from the compound 21.

(3) Utilization of the partial removal of an acyl group by a Grignard reagent

As described above, the compounds 104a and 105a can be obtained from the compound 102a, but I(1,4)P2 can be obtained by subjecting the compound 105a to a phosphorylation, deacylation and desilylation.

When 1,3,5-tribenzoyl-I is reacted with a Grignard reagent, 1,3-tribenzoyl-I and 1,5-dibenzoyl-I can be synthesized, and from these compounds, I(1,3)P$_2$ and I(1,5)P$_2$ can be synthesized.

(4) Of all the above-mentioned myoinositol derivatives having the hydroxyl groups, an optically active compound of a meso from can be selectively obtained from a D- or L-tartaric acid derivative in the same manner as in case that the compound 112 is obtained from the compound 110. Furthermore, a compound which is a racemic modification can be kinetically obtained on the basis of the same principle as in the preparation of the compound D-1 or 119b from the compound DL-1.

Examples of the meso form compound include I,I(1,3)Bz$_2$, I(1,3,5)Bz$_3$, I(1,3,4,6)Bz$_4$, I(1,3)Bz$_2$(4,6)Si$_2$, I(2,4,6)Si$_3$, I(2)Si, I(2,5)Si$_2$ and I(1,3,4,5,6)Bz$_5$.

Examples of the compound which is the racemic modification include I(1)Bz, I(1,4,5)Bz$_3$, I(1,3,4)Bz$_3$, I(1,5)Bz$_2$, I(1,4)Bz$_3$, I(1,5,6)Bz$_3$, I(1,3,6)Si$_3$, I(2,5,6)Si$_3$, I(1,3,4)Bz$_3$, I(2,3,4)Si$_3$ and I(2,3,4,6)Si$_4$.

Examples of the compound having the tartaric acid derivative (T) include I(1,3,5)Bz$_2$(4)T, I(1,4,5)Bz$_3$(3)T, I(1,3,4)Bz$_3$(5)T, I(1,3,4)Bz$_3$(5)T(2,6)Bz$_2$, I(1,4,5)Bz$_3$(3)T(2,6)Bz$_2$ and I(1,3,4,5)Bz$_3$(6)T.

Figure 10:
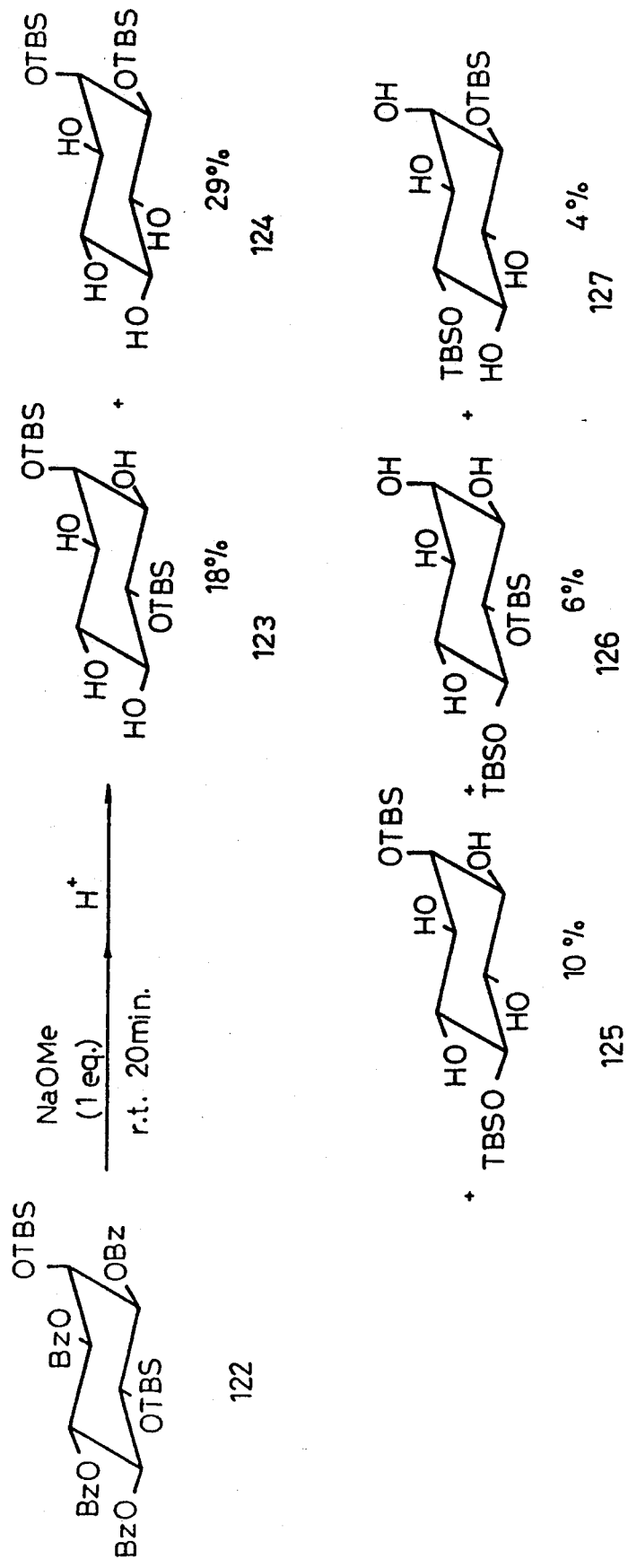
FIG. 10 shows the removal of the benzoyl groups from 2,6-di-O-tert-butyldimethylsilyl-1,3,4,5-tetra-O-benzoylmyoinositol by the use of sodium methoxide.

In FIG. 10, when I(1,3,4,5)Bz$_4$(2,6)Si$_2$ (22) is eliminated by the use of sodium methoxide, the transformation of a TBS (dimethyl-t-butylsilyl) group occurs at times.

In addition to I(2,6)Si$_2$ (23), I(1,2)Si$_2$ (24), I(2,5)Si$_2$ (25), I(5,6)Si$_2$ (26) and I(1,4)Si$_2$ (27) can be obtained from I(1,3,4,5)Bz$_4$(2,6)Si$_2$ (22). The hydroxyl groups of these compounds are then phosphorylated and the silyl groups are eliminated, thereby obtaining I(1,4,5,6)P$_4$, I(1,3,4,6)P$_4$, I(1,2,3,4)P$_4$ and I(1,2,4,5)P$_4$ can be obtained which are difficult to prepare in a conventional manner.

Next, the present invention will be described in reference to examples. It is to be noted that the scope of the present invention should not be limited to these examples.

EXAMPLE 1

Preparation of polybenzoyl-myoinositol

Myoinositol (1) (1.50 g, 8.33 mmol) was suspended in dried pyridine (150 ml) under a nitrogen atmosphere, and benzoyl chloride (3.38 ml, 29.1 mmol) was added thereto at room temperature. The solution was heated up to 90° C. and then stirred for 2 hours. After reaction, ethyl acetate was added to the solution, and this solution was then washed with water, an aqueous saturated potassium hydrogensulfate solution, an aqueous saturated sodium hydrogencarbonate solution, water and an aqueous saturated sodium chloride solution in this order. The organic layer was dried over magnesium sulfate, filtered, and then concentrated, and the resulting residue was recrystallized from methanol in order to obtain a compound (2). The filtrate was treated through a column chromatography (ethyl acetate/hexane = ½ to 2/1) to isolate compounds (3), (4), (5), (6), (7), (8) and (9). Here, since the Rf values of the compounds (3) and (4) were close to each other, they were further purified through a column chromatography (benzene/acetone = 16/1).

Compound (2): 1,3,4,5,6-pentabenzoyl-myoinositol
Yield: 0.79 g (19%)
Rf: 0.8 (ethyl acetate/hexane = 1/1)
Compound (3): 1,3,4,5-tetrabenzoyl-myoinositol
Yield: 1.63 g (37%)
Rf: 0.25 (benzene/acetone = 16/1)
$^1$H-NMR ($\delta$ in CDCl$_3$, 270 MHz), 4.66 (1H; t; J$_{61}$=J$_{65}$=9.77 Hz: H$_6$), 4.73 (1H; t; j$_{21}$=J$_{23}$=2.44 Hz: H$_2$), 5.43 (1H; dd; J$_{12}$=2.44 Hz, J$_{16}$=10.07 Hz:H$_1$), 5.53 (1H; dd; J$_{32}$=2.44 Hz, J$_{34}$=10.37 Hz:H$_3$), 5.66 (1H; t; J$_{56}$=J$_{54}$=9.76 Hz:H$_5$), 6.29 (1H; t; J$_{45}$=J$_{43}$=10.07 Hz:H$_4$), 7.23–7.61 (12H; m. aromatic-H), 7.82–8.13 (8H; m. aromatic-H).

Compound (4): 1,3,4,6-tetrabenzoyl-myoinositol
Yield: 0.64 g (15%)
Rf: 0.20 (benzene/acetone = 16/1)
$^1$H-NMR $\delta$4.19, 4.80, 5.58, 6.22, 7.25–7.52, 7.93–8.02
Compound (5): 1,3,5-tribenzoyl-myoinositol
Yield: 0.61 g (13%)
Rf: 0.45 (ethyl acetate/hexane = 1/1)
$^1$H-NMR 6 4.52, 4.56, 5.39, 5.45, 7.37–7.58, 8.03–8.09
Compound (6): 1,4,5-tribenzoyl-myoinositol
Yield: 0.23 g (4.8%)
Rf: 0.25 (ethyl acetate/hexane = 1/1)
$^1$H-NMR 6 4.04, 4.47, 4.56, 5.25, 5.54, 5.80, 7.22–7.59, 7.85–8.12
Compound (7): 1,3,4-tribenzoyl-myoinositol
Yield: 0.35 g (7.3%)
Rf: 0.20 (ethyl acetate/hexane = 1/1)
$^1$H-NMR 6 3.81, 4.28, 4.58, 5.17, 5.35, 5.93, 7.32–7.67, 7.93–8.18, 4.50
Compound (8): 1,5,6-tribenzoyl-myoinositol
Yield: 0.028 g (0.58%)
Rf: 0.2 (ethyl acetate/hexane = 2/1)
$^1$H-NMR 6 3.88, 4.26, 4.48, 5.33, 5.53, 6.15, 7.16–7.44, 7.73–7.93
Compound (9): 1,5-dibenzoyl-myoinositol
Yield: 0.035 g (0.61%)
Rf: 0.1 (ethyl acetate/hexane = 2/1)
$^1$H-NMR 6 3.69, 4.02, 4.31, 4.34, 5.09, 5.17, 7.41–7.60, 8.08–8.14

EXAMPLE 2

In accordance with the same procedure as in Example 1, benzoyl chloride (3.5 equivalents) was added to myoinositol (1) (1 equivalent) in a dried pyridine solvent under a nitrogen atmosphere, while temperature was changed, and each solution was then stirred for 2 hours, thereby obtaining compounds (2), (3) and (4) in the following yields.

| Reaction temp. (°C.) | (2) | (3) | (4) Yield (%) |
| --- | --- | --- | --- |
| 0 to Room temp. | 48 | 15 | 2.8 |
| Room temp. to 65 | 36 | 38 | 9.7 |

EXAMPLE 3

1,3,4,5-tetrabenzoyl-myoinositol (2.37 g, 3.98 mmol) was dissolved in a solution of dried dichloromethane (40 ml) and dried cyclohexane (20 ml) under a nitrogen atmosphere, and benzyltrichloroacetoimidate (9.50 g, 37.56 mmol) was added thereto at room temperature. Next, trifuloromethanesulfonic acid (0.36 g, 2.39 mmol) was added thereto at room temperature, followed by stirring for 4.5 hours. Several milliliters of pyridine were added thereto so as to quench the acid, and ethyl acetate was added thereto and then washed with an aqueous saturated potassium hydrogensulfate solution, an aqueous saturated sodium hydrogencarbonate solution, water and an aqueous saturated sodium chloride solution in this order. The organic layer was dried over magnesium sulfate, filtered, and then concentrated, and the resulting residue was treated through a column chromatography (ethyl acetate/hexane = 1/4) to isolate 1,3,4,5-tetrabenzoyl-2,6-dibenzyl-myoinositol (10) and 1,3,4,5-tetrabenzoyl-6-benzyl-myoinositol (11).

Compound (10):
Yield: 2.00 g (65%)
Rf: 0.4 (ethyl acetate/hexane = 1/3)
$^1$H-NMR $\delta$4.54, 4.56, 4.60–4.79, 5.48, 4.49, 5.79, 6.26, 6.95–7.63, 7.82–8.05
Compound (11):
Yield: 0.49 g (18%)
Rf: 0.2 (ethyl acetate/hexane = 1/3)
$^1$H-NMR $\delta$4.58, 4.67, 4.69, 5.45, 5.79, 6.22, 6;98–8.12
1,3,4,5-tetrabenzoyl-2,6-dibenzyl-myoinositol (10) (1.89 g, 2.43 mmol) was suspended in dried methanol (30 ml) under a nitrogen atmosphere, and sodium hydride (0.233 g, 9.72 mmol) dissolved in methanol (5 ml) was added thereto, followed by stirring at room temperature for 10 hours. Next, the reaction system was passed through a cation exchange resin (Amberlight IR-120) to neutralize the solution, and this solution was then concentrated. The resulting residue was treated through a column chromatography (dichloromethane/methanol=20/1) to isolate 2,6-dibenzyl-myoinositol (12).

Compound (12):
Yield: 0.304 g (35%)
Rf: 0.45 (ethyl acetate/hexane=10/1)
$^1$H-NMR $\delta$ 3.36, 3.43, 3.56, 3.66, 3.71, 3.97, 4.81–4.93, 7.38–7.44

EXAMPLE 4

Benzene was added to a compound (12) (34.5 mg, 0.0957 mmol), and azeotropy was carried out. Afterward, tetrazole (60.3 mg, 0.8615 mmol) was added thereto, and the solution was suspended in dried methylene chloride (1.5 ml) under a nitrogen atmosphere. Next, 1,5-dihydro-3-diethylamido-2,4,3-benzooxaphosphepine (137.4 mg, 0.5743 mmol) was added thereto at room temperature, followed by stirring for 20 minutes. After post-treatment, the solution was purified through a thin-layer chromatography in order to obtain 2,6-dibenzylmyoinositol-1,3,4,5-tetraphosphoric acid (13).

Compound (13):
Yield: 93.5 mg (90%)
Rf 0.5 (ethyl acetate/hexane=10/1)
$^1$H-NMR $\delta$ 4.18, 4.52, 4.68, 4.74–5.57, 7.08–7.42.

Methanol was added to and dissolved in the compound (13), and one spatula of 10% palladium carbon was added thereto. The solution was then stirred, and hydrogen substitution was performed under reduced pressure The solution was stirred at room temperature for 17 hours, filtered, concentrated, and then purified through a cellulose column chromatography (propanol/ammonia/water=5/5/1) in order to obtain myoinositol-1,3,4,5-tetraphosphoric acid.

Yield: 20.9 mg (84%)
Rf: 0.16 (propanol/ammonia/water=5/5/1)

EXAMPLE 5

Following the same procedure as in Example 2, 50 mg of 1,4,5-tribenzoyl-myoinositol was reacted with benzyl trichloroacetoimidate to obtain 35 mg of 1,4,5-tribenzoyl-2,3,6-tribenzyl-myoinositol. This was then treated with sodium methylate, as in Example 3, in order to obtain 12 mg of 2,3,6-tribenzyl-myoinositol which was a known compound.

EXAMPLE 6

Phosphorylation of 2,3,6-tribenzyl-myoinositol

Phosphepine (169.5 mg, 0.708 mmol) was added to a mixture of 2,3,6-tri-O-benzyl-myoinositol (66.8 mg, 0.148 mmol) and 1H-tetrazole (74.0 mg, 1.056 mmol) in the solvent of anhydrous methylene chloride (1.5 ml) at room temperature under a nitrogen atmosphere in a 10-ml Hertznas. After 10 minutes, the disappearance of the materials was confirmed, and water (50 μl, 18.7 mmol) was then added thereto so as to break excessive phosphepine. After stirring for 10 minutes, the solution was cooled at −40° C. for 10 minutes, and m-chloroperbenzoic acid (mCPBA, 221.8 mg, 1.03 mmol) and then added thereto. Ten minutes after the temperature of the solution had been returned to room temperature, ethyl acetate was added thereto, and then washed with a 10% sodium sulfite, an aqueous saturated sodium hydrogencarbonate solution, water and an aqueous saturated sodium chloride solution in this order. The organic layer was separated, dried over anhydrous sodium sulfate, filtered, and then passed through a column chromatography to isolate the desired product.

Yield: 143.5 mg (97%)
IR (CHCl$_3$) 1010 P-O-C; 1200 P=0
$^1$H-NMR $\delta$ 3.56, 4.21, 4.40, 4.60, 4.63–5.30, 5.41–5.65, 7.06–7.44

EXAMPLE 7

Following the same procedure as in Example 6, 3,4,5,6-tetrabenzyl-myoinositol was phosphorylated in order to obtain 3,4,5,6-tetrabenzyl-1,2-bis(1',5'-dihydro-3'-oxo-2',4',3'-benzodioxaphosphepinyl)-myoinositol.

Yield: 91%
IR (CHCl$_3$) 1000 P-O-C, 1200 P=0
$^1$H-NMR $\delta$ 3.56–3.63, 3.89, 3.96, 4.59, 4.64, 4.79–5.39, 5.38, 5.55, 7.14–7.42

EXAMPLE 8

The same procedure as in Example 6 was effected in order to obtain 1,2-cyclohexylidene-3,4,5,6-tetrakis-(1',5'-dihydro-3'-oxo-2',4',3'-benzodioxaphosphepinyl)-myoinositol from 1,2-cyclohexylidenemyoinositol.

Yield: 82%
IR (CHCl$_3$) 1015 P-O-C, 1200 P=0
$^1$H-NMR $\delta$ 1.38–1.96, 4.39, 4.75, 4.80–5.16, 5.26–5.69, 7.25–7.38

EXAMPLE 9

Preparation of
3,6-dibenzyl-2-benzoyl-4,5-bis(dibenzylphosphoryl)-1-(1',5'-dihydro-3'-thio-2',4',3'-benzodioxaphosphepinyl)-myoinositol 1-tetrazole (6.33 mg, 0.0904 mmol) was added to a methylene chloride solution of 3,6-dibenzyl-2-benzoyl-4,5-bis(dibenzylphosphoryl)myoinositol (29.7 mg, 0.030 mmol), and diethylaminophosphepine (10.8 mg, 0.0452 mmol) was further added thereto, followed by stirring. After the disappearance of the materials had been confirmed by TLC, sulfur (2.90 mg, 0.0704 mmol) was added, followed by stirring at room temperature overnight. A post-treatment was then performed to obtain the desired product.

Yield: 29.6 mg (83%)
Rf: 0.5 (ethyl acetate/hexane=1/1)
$^1$H-NMR $\delta$ 8.91–8.01, 7.66–7.00, 6.23, 4.72, 4.20, 5.23–4.52

EXAMPLE 10

Preparation of
3,4,5,6-tetrabenzyl-1-(1',5'-dihydro-3'-thio-2',4',3'-benzodioxaphosphepienyl)-myoinositol 1-tetrazole (204.6 mg, 2.92 mmol) was added to a methylene chloride solution of 3,4,5,6-tetrabenzyl-myoinositol (263.0 mg, 0.486 mmol), and diethylaminophosphepine (349.3 mg, 1.46 mmol) was further added thereto, followed by stirring for 30 minutes. A post-treatment was performed to obtain the desired product.

Yield: 410.3 mg (90%)
Rf: 0.3 (ethyl acetate/hexane=1/4)
$^1$H-NMR $\delta$ 7.47–7.11, 5.63, 4.8–4.9, 3.96, 3.87, 3.58, 3.56, 3.59, 5.5–4.5 31P-NMR $\delta$ 73.009, 72.841, 72.841

EXAMPLE 11

Preparation of 2,3,6-tribenzyl-1,4,5-tris(1',5'-dihydro-3'-thio-2',4',3'-benzodioxaphosphepinyl)myoinositol 1-tetrazole (47.4 mg, 0.677 mmol) was added to a methylene chloride solution of 2,3,6-tribenzyl-myoinositol (33.9 mg, 0.0752 mmol), and diethylaminophosphepine (81.1 mg, 0.339 mmol) was further added thereto, followed by stirring for 30 minutes. Sulfur (21.7 mg, 0.677 mmol) was added, followed by stirring overnight. A post-treatment was then performed to obtain the desired product.

Yield: 58.3 mg (74%)
Rf: 0.8 (ethyl acetate/hexane=1/1)
$^1$H-NMR $\delta$7.47–7.00, 5.60–5.48, 4.49, 4.20, 3.56, 5.35–4.57

EXAMPLE 12

Synthesis of 1,5-dihydro-3-diisopropylamino-2,4,3-benzodioxaphosphepine

Phthalyl alcohol (1.15 g, 8.31 mmol) was dissolved in 5 ml of THF, and bisdiisopropylaminochlorophosphine (2.21 g, 8.31 mmol) which was dissolved in 5 ml of THF was added dropwise to the solution at $-15°$ C. under a nitrogen atmosphere. Afterward, the temperature of the solution was adjusted to room temperature, and after the disappearance of phthalyl alcohol had been confirmed, hydrochloride of diisopropylamine was washed with ether. The wash liquor was concentrated and then distilled in order to obtain the desired product having a melting point of from 150° to 155° C. (0.7 mmHg).

Yield: 777 mg (35%)
IR: 1020 (P-O-C, P-N) 970 (P-O-C, P-N)
$^1$H-NMR $\delta$1.20, 3.65, 4.89, 5.10, 7.23

EXAMPLE 13

Preparation of 1,5-dihydro-3-phenethyloxy-2-oxo-2,4,3-benzodioxaphosphepine $\beta$-phenethyl alcohol (18.89 mg, 0.155 mmol) and H-tetrazole (34.47 mg, 0.492 mmol) were added to 1 ml of dried methylene chloride, and the solution was then dissolved in 1 ml of methylene chloride at room temperature under a nitrogen atmosphere. Afterward, a subphosphorylating agent (62.15 mg, 0.233 mmol) was added dropwise thereto. After the disappearance of $\beta$-phenethyl alcohol had been confirmed, mCPBA (0.328 mmol) was added thereto at $-40°$ C., and the temperature of the solution was then adjusted to room temperature. A post-treatment was performed to obtain the desired product.

Yield: 40.1 mg (85%)
IR: 1200 (P=C), 1000 (P-O), 900 (P-O)
$^1$H-NMR $\delta$3.60, 4.38, 5.02, 5.08, 7.15

EXAMPLE 14

Diethylaminophosphepine (108.3 mg, 0.453 mmol) was added to a mixture of trans-1,2-cyclohexanediol (16.8 mg, 0.145 mmol) and 1H-tetrazole (63.3 mg, 0.904 mmol) in a solvent of methylene chloride (1.5 ml) at room temperature under a phosphorylating nitrogen atmosphere of trans-1,2-cyclohexanediol in a 10-ml Hertznas, followed by stirring for 10 minutes. Afterward, mCPBA was further added thereto at $-40°$ C., and the solution was then stirred at room temperature for 10 minutes. A post-treatment was performed to obtain the desired product.

Yield: 61.4 mg (88%)
IR: 1020 (P-O-C), 1270 (P=O)
$^1$H-NMR $\delta$1.23–2.43, 4.51–4.52, 5.01–5.38 7.18–7.35

EXAMPLE 15

Phosphorylation of trans-1,2-cyclohexanediol and oxidization with sulfur

Diethylaminophosphepine was added to a mixture of trans-1,2-cyclohexanediol (54.7 mg, 0.47 mmol) and 1H-tetrazole (195.6 mg, 2.792 mmol) in the solvent of methylene chloride (1.5 ml) at room temperature under a nitrogen atmosphere in a 10-ml Hertznas, followed by stirring for 10 minutes. Afterward, sulfur was added to the solution, and this solution was then stirred overnight. A post-treatment was performed to obtain the desired product.

Yield: 206.1 mg (85%)
IR: 1000 (P-O-C)
$^1$H-NMR $\delta$1.24–2.43, 4.67–4.73, 5.08–5.42 7.12–7.37

EXAMPLE 16

Preparation of 1,5-dihydro-1,5-dimethyl-3-diethylamino-2,4,3-benzodioxaphosphepine 1,2-bis($\alpha$-hydroxyethyl)benzene (886 mg, 5.39 mmol) was placed in a 10-ml flask, and the atmosphere in the flask was replaced with nitrogen.

Afterward, hexaethylphosphorus triamide (2.08 ml, 7.55 mmol) was injected into the flask. The solution was heated under reflux at 100° C. for 1 hour in order to obtain a colorless oily material. This reaction mixture was distilled under a reduced pressure of 0.5 mmHg by the use of a Kugelroa.

As a result, 835.5 mg (58%) of a fraction having a boiling point of from 130° to 150° C. was obtained.

EXAMPLE 17

Reaction of 1,5-dihydro-1,5-dimethyl-3-diethylamino-2,4,3-benzodioxaphosphepine with phenethyl alcohol In a 10-ml egg-plant type flask were placed phenethyl alcohol (41.64 mg, 0.34 mmol) and tetrazole (62.1 mg, 0.89 mmol), and the atmosphere in the flask was replaced with nitrogen. 2 ml of dried $CH_2Cl_2$ was introduced thereinto. The phosphorylating agent (118.5 mg, 0.44 mmol) obtained in Example 16 was injected thereinto, and the solution was stirred at room temperature for 50 minutes. Next, the solution was cooled to $-40°$ C., and mCPBA (117.7 mg, 0.68 mmol) dissolved in 1.5 ml of $CH_2Cl_2$ was introduced thereinto, followed by stirring at room temperature for 30 minutes. A post-treatment was performed to obtain the desired product.

Yield: 77.4 mg (68%)
$^1$H-NMR $\delta$1.71, 2.92, 4.25, 5.51, 5.76, 7.25
P-NMR-1.7

EXAMPLE 18

Preparation of 2,6-bis(dimethyl-t-butylsilyl)-1,3,4,5-tetrabenzoyl-myoinositol (102a)

A compound 101 (1.096 g, 1.837 mmol) was dissolved in anhydrous methylene chloride (20 ml) under a nitrogen atmosphere, and 2,6-lutidine (1.28 ml, 11.0 mmol) was added thereto. The solution was cooled to 0° C., and t-butyl-dimethylsilyl-trifluoromethane sulfonate (1.69 ml, 7.35 mmol) was added dropwise thereto little by little. After 12 hours, ethyl acetate was added thereto and then washed with an aqueous saturated potassium hydrogensulfate solution, an aqueous saturated sodium hydrogencarbonate solution, water and an aqueous saturated sodium chloride solution in this order twice in each washing step. The organic layer was dried over anhydrous magnesium sulfate, filtered, and then concentrated, and the resulting residue was recrystallized from methanol in order to obtain 1.40 g of a compound 102a [yield=92%, Rf value=0.64 (ethyl acetate/hexane=1/23), m.p.=182.5 to 183° C.].

EXAMPLE 19

Preparation of 2,6-bis(triethylsilyl)-1,3,4,5-tetrabenzoylmyoinositol (102b):

The compound 101 (256.9 mg, 0.5216 mmol) and imidazole (248.6 mg, 3.65 mmol) which had been dried by azeotropy with anhydrous benzene were dissolved in anhydrous dimethylformamide (5 ml) under a nitrogen atmosphere, and triethylsilyl chloride (314 mg, 2.09 mmol) was added thereto at room temperature, followed by stirring for 3 hours. Afterward, ethyl acetate was added thereto, and then washed with an aqueous saturated potassium hydrogensulfate solution, an aqueous saturated sodium hydrogencarbonate solution, water and an aqueous saturated sodium chloride solution in this order twice in each washing step. The organic layer was dried over anhydrous magnesium sulfate, filtered, and then concentrated, and the resulting residue was recrystallized from methanol in order to obtain 334.8 mg of a compound 102b [yield=89%, Rf value=0.64 (ethyl acetate/hexane=⅓), m.p.=162° to 163° C.].

EXAMPLE 20

Preparation of 2,6-bis(dimethyl-t-butylsilyl)myoinositol (103a) and 2,6-bis(dimethyl-t-butylsilyl)-3-benzoyl-myoinositol (104a)

35.6 ml (28.4 mmol) of a Grignard reagent (whose total volume was brought into 30 ml by the use of an ether solvent and whose yield was regarded as 80%) which had been prepared from ethyl bromide (4.48 ml, 60.0 mmol) and metallic magnesium (1.46 g, 60.0 mmol) was added to an anhydrous ether solution (10 ml) of the compound 102a (1.304 g, 1.580 mmol), followed by stirring under reflux for 1 hour. An aqueous saturated potassium hydrogensulfate solution was added thereto little by little under cooling at −40° C. Afterward, ethyl acetate was added thereto, and then washed with an aqueous saturated potassium hydrogensulfate solution, water and an aqueous saturated sodium chloride solution twice in each washing step. The organic layer was dried over anhydrous magnesium sulfate, filtered, and then concentrated, and the resulting residue was purified through a column chromatography (ethyl acetate/hexane=2:3), thereby obtaining 538 mg of a compound 103a [yield=83%, Rf value=0.18 (ethyl acetate/hexane=2/3)] and 38.7 mg of a compound 104a [yield 5%, Rf value=0.24 j(ethyl acetate/hexane=2/3)] (transparent and oily).

NMR: Compound 103a $^1$H(CDCl$_3$), δ=0.02, 0.80, 3.08, 3.21, 3.24, 3.49, 3.59, 3.97. Compound 104a $^1$H(CDCl$_3$), δ=−0.07, 0.05, 0.75, 2.30, 2.60, 2.85, 3.46, 3.62, 3.83, 4.17, 4.31, 5.00, 7.4–7.6 (3H), 8.1 (2H).

EXAMPLE 21

2,6-bis(triethylsilyl)-myoinositol (103b) and 2,6-bis(triethylsilyl)-3-benzoylmyoinositol (104b)

5.5 ml (4.4 mmol) of the Grignard reagent prepared in Example 20 was added to an anhydrous ether solution (1 ml) of the compound 102b (208.4 mg, 0.2526 mmol), and the solution was then stirred under reflux for 1 hour. The same procedure as in Example 20 was effected, thereby obtaining 82.3 mg of a compound 103b [yield=80%, Rf value =0.18 (ethyl acetate/hexane=2/3)] and 4.5 mg of a compound 104b [yield=3%, Rf value=0.24 ethyl acetate/hexane=2/3)] (transparent and oily).

NMR: Compound 103b $^1$H(CDCl$_3$), δ=0.68, 0.685, 0.977, 2.17, 2.40, 2.69, 3.03, 3.2–3.4 (3H, 3.6–3.8 (2H), 4.16. Compound 104b $^1$H(CDCl$_3$), δ=0.52–0.62 (12H), 0.87 (9H), 0.92 (9H), 2.35, 2.69, 2.93, 3.44, 3.59, 3.83, 4.18, 4.33, 4.97, 7.4–7.6 (3H), 8.1 (2H).

EXAMPLE 2

2,6-bis(dimethyl-t-butylsilyl)myoinositol (103a) and 2,6-bis(dimethyl-t-butylsilyl)-3-benzoyl-myoinositol (104a)

0.94 ml (0.76 mmol) of the Grignard reagent prepared in Example 20 was added to an anhydrous ether solution (2 ml) of the compound 102b (94.5 mg, 0.1145 mmol) at room temperature, followed by stirring for 12 minutes. Afterward, the same procedure as in Example 20 was effected in order to obtain 15.8 mg (yield=34%) of a compound 103a and 31.1 mg (yield=53%) of a compound 104a in a predominant amount.

EXAMPLE 23

2,6-bis(triethylsilyl)-myoinositol (103b) and 2,6-bis(triethylsilyl)-3-benzoylmyoinositol (104b)

13 ml (10.4 mmol) of a Grignard reagent (whose total volume was brought into 30 ml by the use of an ether solvent and whose yield was regarded as 80%) which had been prepared from methyl iodide (2.4 mg, 30 mmol) and metallic magnesium (731 mg, 30 mmol) was added to anhydrous ether solution (5 ml) of a compound 102b (413.6 mg, 0.519 mmol) at room temperature, followed by stirring for 1 hour. Afterward, the same procedure as in Example 20 was effected, thereby obtaining 54.4 mg (28%) of a compound 103b and 128 mg (51%) of a compound 104b.

EXAMPLE 24

Preparation of 2,6-bis(dimethyl-t-butylsilyl)-1,3,4,5-tetrakis(1,5-dihydro-2',4',3'-benzodioxaphephepinyl)myoinositol (106a)

The compound 103a (87.0 mg, 0.213 mmol) was dissolved in anhydrous methylene chloride (2 ml) under a nitrogen atmosphere, and tetrazole (179 mg, 2.55 mmol) was then suspended therein. Next, 1,5-dihydro-3-diethylamino-2,4,5-benzodioxaphosphepine (408 mg, 1.70 mmol) was added thereto at room temperature, followed by stirring for 1 hour. In order to break the excessive amount of the phosphepine, water (406 μl, 1.70 mmol) was added thereto at room temperature, followed by stirring for 1 hour. The solution was then cooled to −40° C., and m-chloroperbenzoic acid (441 mg, 2.56 mmol) was added thereto at room temperature, followed by stirring for 1 hour. Ethyl acetate was added thereto, and then washed with a 10% aqueous sodium sulfite solution, an aqueous saturated sodium hydrogencarbonate solution, water, an aqueous saturated sodium chloride solution in this order twice in each washing step. The organic layer was dried over anhydrous sodium sulfate, filtered, and then concentrated, and the resulting residue was purified through a thin layer chromatography (methylene chloride/methanol =20:1), thereby obtaining 228 mg of a compound 106a [yield=94%, Rf value=0.53 (methylene chloride/methanol =20/1), melting point=179°–181° C.].

NMR: Compound 106a δ=−0.06–0.15 (2H), 0.78–0.95 (18H). 4.40–5.65 (18H), 7.12–7.39 (12H).

EXAMPLE 25

Preparation of 2,6-bis(triethylsilyl)-1,3,4,5-tetrakis(1,5-dihydro-2',4',3'-benzodioxaphosphenyl)myoinositol (106b)

The same procedure as in Example 24 was effected except that a compound 103b (81.3 mg, 0.199 mmol), tetrazole (167 mg, 2.39 mmol), phosphepine (380.7 mg, 159 mmol), water (143 μl, 7.96 mmol) and m-chloroperbenzoic acid (412 mg, 2.39 mmol) were used, in order to obtain 203.9 mg of a compound 106b [yield=90%, Rf value=0.53 (methylene chloride/methanol=20:1)] (oily).

NMR: IR 1270, 1250, 1200, 1160, 1120, 1000, 830, 740, 650

EXAMPLE 26

Preparation of 2,6-bis(triethylsilyl)-3-benzoyl-1,4,5-tris(1',5'-dihydro-2',4',3'-benzodioxaphosphepinyl)myoinositol (107b)

The same procedure as in Example 24 was effected except that a compound 104b (40.7 mg, 0.0840 mmol), tetrzole (42.1 mg, 0.588 mmol), phosphepine (100.4 mg, 0.420 mmol), water (31.0 μl, 1.68 mmol) and m-chloroperbenzoic acid (116 mg, 0.617 mmol) were used, in order to obtain 69.6 mg of a compound 107b [yield=81%, Rf value=0.36 (methylene chloride/methanol=20/1), m.p.=158°–154° C.].

EXAMPLE 27

Preparation of a 2K salt (108) of myoinositol-1,3,4,5-tetraphosphoric acid

A compound 106b (130 mg, 0.114 mmol) was suspended in a mixed solvent of methanol (2.5 ml) and water (0.6 ml), and 5% palladium carbon (130 mg) was then added thereto, followed by hydrogen substitution. The solution was stirred at room temperature for 6 hours, filtered, concentrated, and then purified through a cellulose column chromatography (i-propanol:aqueous ammonia:water=5:5:1). Next, the solution was passed through Dowex 50WX-2 (pyridinium type) and Dowex 50W-X2 (potassium type) in order to obtain 74 mg of a compound 108 [quantitative, Rf value=0.23 (n-PrOH/NH$_4$OH/H$_2$O=5/5/1)].

EXAMPLE 28

Preparation of a 3K salt (109) of myoinositol-1,4,5-triphosphoric acid

A compound 107b (69.9 mg, 0.0660 mmol) was suspended in a mixed solvent of methanol (1.2 ml) and water (0.3 ml), and 5% palladium carbon (70 mg) was added thereto, followed by hydrogen substitution The solution was stirred at room temperature for 6 hours, filtered, concentrated, dried sufficiently, and then dissolved in anhydrous methanol. Afterward, sodium hydride (15.8 mg, 0.66 mmol) was added thereto under cooling at 0° C., followed by stirring at room temperature for one day. The water layer was separated by the use of ethyl acetate and water, and then concentrated, and the resulting residue was passed through Dowex 50W-X$_2$ (pyridine type) and then purified through a cellulose column chromatography (MeOH:NH$_4$OH:H$_2$O=5:4:1). Next, the solution was further passed through Dowex 50W-X2 (pyridine type) and then Dowex 50W-X2 (potassium type) in order to obtain 35 mg of a compound 109 [quantitative, Rf value=0.2 (MeOH/NH$_4$OH/H$_2$O=5:4:1)].

EXAMPLE 29

Preparation of 1,3,5-tribenzoylmyoinositol (110)

Myoinositol (3.0 g, 16.7 mmol) was suspended in anhydrous pyridine (100 ml) under a nitrogen atmosphere, and then heated up to 90° C. Next, benzoyl chloride (3.9 ml, 27.8 mmol) was added dropwise thereto, followed by stirring for 1 hour. Pyridine was distilled off under reduced pressure, and ethyl acetate was then added thereto. The solution was washed with an aqueous saturated potassium hydrogensulfate solution, an aqueous saturated sodium hydrogencarbonate and an aqueous saturated sodium chloride solution, and the organic layer was then dried over sodium sulfate. After concentration, the resulting residue was purified through a silica gel column chromatography (ethyl acetate/methylene chloride=1:6), and then recrystallized from benzene, thereby obtaining 1.22 g of a compound 110 [yield=15%, Rf value =0.3 (ethyl acetate:CH$_2$Cl$_2$=1:6), m.p.=133°–135° C.].

EXAMPLE 30

Preparation of 1,3,5-tribenzoyl-4-(methyl-2',3'-O-cyclohexylidene-D-tartaroyl)myoinositol (112b)

2,3-O-cyclohexylidene-D-tartaric acid monomethyl ester 111b (44.9 mg, 0.184 mmol) was subjected to azeotropy with benzene, and it was dissolved in anhydrous tetrahydrofuran (1.5 ml) under a nitrogen atmosphere and then cooled to 0° C. Next, methanesulfonyl chloride (15.7 μl, 0.202 mmol) and N-methylmorpholine (50.6 μl, 0.460 mmol) were added thereto, followed by stirring for 10 minutes. Afterward, a compound 110 (45.3 mg, 0.092 mmol) and the catalytic amount of 4-dimethylaminopyridine were added thereto, followed by stirring for 3 hours. Ethyl acetate was added, and then washed with an aqueous saturated potassium hydrogensulfate solution, an aqueous saturated sodium hydrogencarbonate and an aqueous saturated sodium chloride solution, and the organic layer was then dried over sodium sulfate. After concentration, the resulting residue was purified through a thin-layer chromatography (benzene:acetone=7:1), thereby obtaining 37.4 mg of a compound 112b [yield=57%, Rf value=0.5 (benzene:acetone:=7:1)] (colorless and oily).

NMR: Compound 112b δ=1.13–1.6 (10H), 2.70, 2.90, 3.50, 4.43, 4.57, 4.69, 5.42, 5.59, 6.12, 7.36–7.6 (9H), 7.94–8.10 (6H).

EXAMPLE 31

Preparation of 1,3,5-tribenzoyl-4-(methyl-2',3'-O-isopropylidene-D-tartaroyl)-myoinositol (112a)

2',3'-O-isopropylidene-D-tartaric acid monomethyl ester (111a) 433.8 mg, 2.12 mmol) was subjected to azeotropy with benzene, dissolved in anhydrous tetrahydrofuran (8.0 ml) under a nitrogen atmosphere, and then cooled to 0° C. Next, methanesulfonyl chloride (180.5 μl, 2.33 mmol) and N-methylmorpholine (582.7 μl, 5.30 mmol) were added thereto, followed by stirring for 10 minutes. Afterward, a compound 102 (522.0 mg, 1.06 mmol) and the catalytic amount of 4-dimethylaminopyridine were added thereto, followed by stirring for 3 hours. Ethyl acetate was then added thereto, and the solution was washed with an aqueous saturated potassium hydrogensulfate solution, an aqueous saturated sodium hydrogencarbonate and an aqueous saturated sodium chloride solution, and the organic layer was then dried over sodium sulfate. After concentration, the resulting residue was purified through a silica gel column chromatography (benzene:acetone=15:1), thereby obtaining 458.5 mg of a compound 112a [yield=64%, Rf value=0.4 (benzene:acetone:=7:1), diastereomer ratio D:L=94.6 (92% de)] (colorless and oily).

NMR: Compound 112a $\delta$=1.11 (3H), 1.29 (3H), 3.5 (3H), 4.44 (2H), 4.58, 4.70, 5.40, 5.42, 5.57, 6.12, 7.40-7.62 (9H), 7.96-8.12 (6H).

EXAMPLE 32

Preparation of 1,3,5-tribenzoyl-4-(methyl-2',3'-O-cyclohexylidene-D-tartaroyl)myoinositol (112b)

A compound 111b (42.3 mg, 0.164 mmol) was subjected to azeotropy with benzene, and it was dissolved in anhydrous tetrahydrofuran (1.5 ml) under a nitrogen atmosphere and then cooled to 0° C. Next, methanesulfonyl chloride (13.9 μl, 0.180 mmol) and N-methylmorpholine (45.1 μl, 0.410 mmol) were added thereto, followed by stirring for 10 minutes. Afterward, a compound 102 (40.4 mg, 0.082 mmol) and the catalytic amount of 4-dimethylaminopyridine were added thereto, followed by stirring for 3 hours. Ethyl acetate was then added, and the solution was washed with an aqueous saturated sodium hydrogensulfate solution, an aqueous saturated sodium hydrogencarbonate solution and an aqueous saturated sodium chloride solution. The resulting residue was purified through a thin-layer chromatography (benzene:acetone=7:1), thereby obtaining 24.7 mg of a compound 112b [yield=42%, Rf value=0.5 (benzene:acetone:=7:1), diastereomer ratio D:L=97.3 (94% de)] (colorless and oily).

EXAMPLE 33

Preparation of 2,6-dibenzyl-1,3,5-tribenzoyl-4-(methyl-2',3'-O-cyclohexylidene-D-tartaroyl)myoinositol (113b) and 6-benzyl-1,3,5-tribenzoyl-4-(methyl-2',3'-cyclohexylidene-D-tartaroyl)myoinositol (114b)

A compound 112b (322.6 mg, 0.486 mmol) was dissolved in a mixture of 3.0 ml of anhydrous methylene chloride and 1.5 ml of anhydrous cyclohexene under a nitrogen atmosphere, and benzyl trichloroacetoimidate (625.4 μl, 3.60 mmol) and trifluoromethanesulfonic acid (26.0 μl, 0.292 mmol) were added thereto under a nitrogen stream, followed by stirring for 4 hours. An aqueous saturated sodium hydrogencarbonate solution was added thereto for quench, and ethyl acetate was then added thereto, followed by washing with water and an aqueous saturated sodium chloride solution. The organic layer was dried over sodium sulfate and then concentrated, and the resulting residue was purified through a silica gel column chromatography (benzene:acetone=25:1) in order to obtain 395.7 mg of a compound 113b [yield=52%, Rf value=0.6 (benzene:acetone=7:1)] and 101 mg of a compound 114b [yield 26%, Rf value=0.5 (benzene:acetone =7:1)] (both were colorless and oily).

NMR: Compound 113a $\delta$=1.12-1.62 (10H), 3.56 (3H), 4.49, 4.51, 4.62, 4.69, 5.16, 5.34, 5.42, 6.09, 6.95-7.65 (19H). 7.94-8.13 (6H).

EXAMPLE 34

Preparation of D-2,6-dibenzyl-myoinositol (115)

A compound 113b (169.2 mg, 0.188 mmol) was suspended in 2.01 mg of anhydrous methanol under a nitrogen atmosphere, and a solution prepared from 1.0 ml of anhydrous methanol and sodium hydride (27.1 mg, 1.13 mol) was added thereto at room temperature, followed by stirring for 10 hours. Next, the reaction solution was passed through a cation exchange resin (Amberlight IR-120 H+ type) to neutralize the solution, and this solution was then concentrated. The resulting residue was treated through a thin-layer chromatography (methylene chloride:methanol=15:1) to obtain 20.4 mg of a compound 115 [yield=31%, Rf value=0.3 ($CH_2Cl_2$:$CH_3OH$=15:1)]. Furthermore, this was recrystallized from methylene chloride in order to obtain an optically pure compound 115. $[\alpha]_D$=29.2 (C=0.65, EtOH), m.p. 146.0°-147.0° C.

EXAMPLE 35

Preparation of 1,3,5-tribenzoyl-2,6-bis(triethylsilyl)-4-(methyl-2',3'-O-isopropylidene-tartaroyl)-D-myoinositol (116a)

A compound 112a (82.1 mg, 0.121 mmol) was dissolved in anhydrous dimethylformamide (1.5 ml) under a nitrogen atmosphere, and imidazole (67.8 mg, 0.966 mmol) and triethylsilyl chloride (95.2 μl, 0.960 mmol) were added thereto, followed by stirring at room temperature for 3 hours. Ethyl acetate was added thereto, and then washed with an aqueous saturated potassium hydrogensulfate solution, an aqueous saturated sodium hydrogencarbonate solution, water and an aqueous saturated sodium chloride solution twice in each washing step. The organic layer was dried over anhydrous sodium sulfate, filtered, and then concentrated, and the resulting residue was purified through a thin-layer chromatography (ethyl acetate/hexane =½) in order to obtain 75.1 mg of a compound 116a [yield=68%, Rf value=0.52 (AcOEt/Hx=½)].

EXAMPLE 36

Preparation of D-2,6-bis(triethylsilyl)myoinositol (117) and D-2,6-bis(triethylsilyl)-3-benzoyl-myoinositol (118)

A compound 116a (113.6 mg, 0.1252 mmol) was dissolved in anhydrous ether (1 ml) under a nitrogen atmosphere, and 4.7 ml (3.76 mmol) of a Grignard reagent (whose total volume was brought into 30 ml by the use of an ether solvent and whose yield was regarded as 80%, i.e., which was used as a 0.8 N solution) which had been prepared from metallic magnesium (729 mg, 30 ml) and ethyl bromide (3.27 g, 30 mmol) was added thereto, followed by stirring under reflux for 1 hour. The solution was cooled to −40° C., and an aqueous saturated potassium hydrogensulfate solution was added thereto little by little. Ethyl acetate was added thereto, and then washed with an aqueous saturated potassium hydrogensulfate solution, water and an aqueous saturated sodium chloride solution twice in each washing step. The organic layer was dried over anhydrous sodium sulfate, filtered, and then concentrated, and the resulting residue was purified through a thin-layer chromatography (ethyl acetate/hexane=½) in order to obtain 39.8 mg of a compound 117 [yield=78%, Rf value=0.11 (AcOEt/Hx =½)] and 8.8 mg of a compound 118 [yield=14%, Rf value=0.16 (AcOEt/HX=½)].

Possibility of Industrial Utilization

According to the present invention, myoinositol polyphosphoric acid can easily be obtained via the intermediate of polyacylmyoinositol by a simple process. When the compound (I) of the present invention is used, the phosphorylation of myoinositol can easily be achieved in a high yield.

In addition, according to the process of the present invention, myoinositol polyphosphoric acid, optically active myoinositol polyphosphoric acid and other myoinositol derivatives can easily be synthesized.

Moreover, it is expected that the myoinositol derivatives will be utilized as medicines.

We claim:

1. A compound selected from the group consisting of 1,3,4,5,6-pentaacylmyoinositol, 1,3,4,5-tetraacylmyoinositol, 1,3,5-triacylmyoinositol, 1,4,5-triacylmyoinositol, 1,3,4-triacylmyoinositol, 1,5,6-triacylmyoinositol or 1',5-diacylmyoinositol.

2. A compound selected from the group consisting of 2,6-bis(dimethyl-t-butylsilyl)-1,3,4,5-tetrabenzoylmyoinositol, 2,6-bis(triethylsilyl)-1,3,4,5-tetrabenzoylmyoinositol, polysilylmyoinositol or 2,6-bis(dimethyl-t-butyl)-3-benzoylmyoinositol.

3. A compound in which the hydroxyl group of myoinositol or its derivative is bonded to the carboxyl group of 2,3-O-alkylidene tartaric acid monoester or 2,3-O-silylidene tartaric acid monoester by an ester bond.

4. A process for preparing myoinositol polyphosphoric acid from polyacyl myoinositol which process comprises the steps of:
(a) protecting the non-acylated hydroxy radical of polyacyl myoinositol with a protecting group removable by hydrogen reduction or with a silylating agent;
(b) de-acylating the protected polyacyl myoinositol;
(c) phosphorylating the thus formed hydroxyl group with a phosphorylating agent; and thereafter
(d) reducing the phosphorylating agent with hydrogen or catalytically reducing the phosphorylating agent with palladium to form myoinositol polyphosphoric acid.

5. The process of claim 4 wherein the phosphorylating agent is a 1,5-dihydro-3-dialkylamino-2,4,3-benzodioxaphosphepine represented by the formula (I)

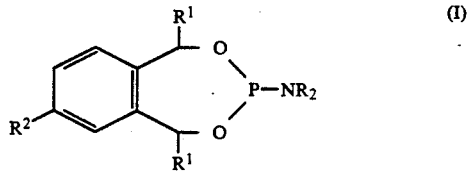

wherein R is lower alkyl, R¹ is hydrogen or lower alkyl, and R² is hydrogen or methoxy.

* * * * *